Figure 1:
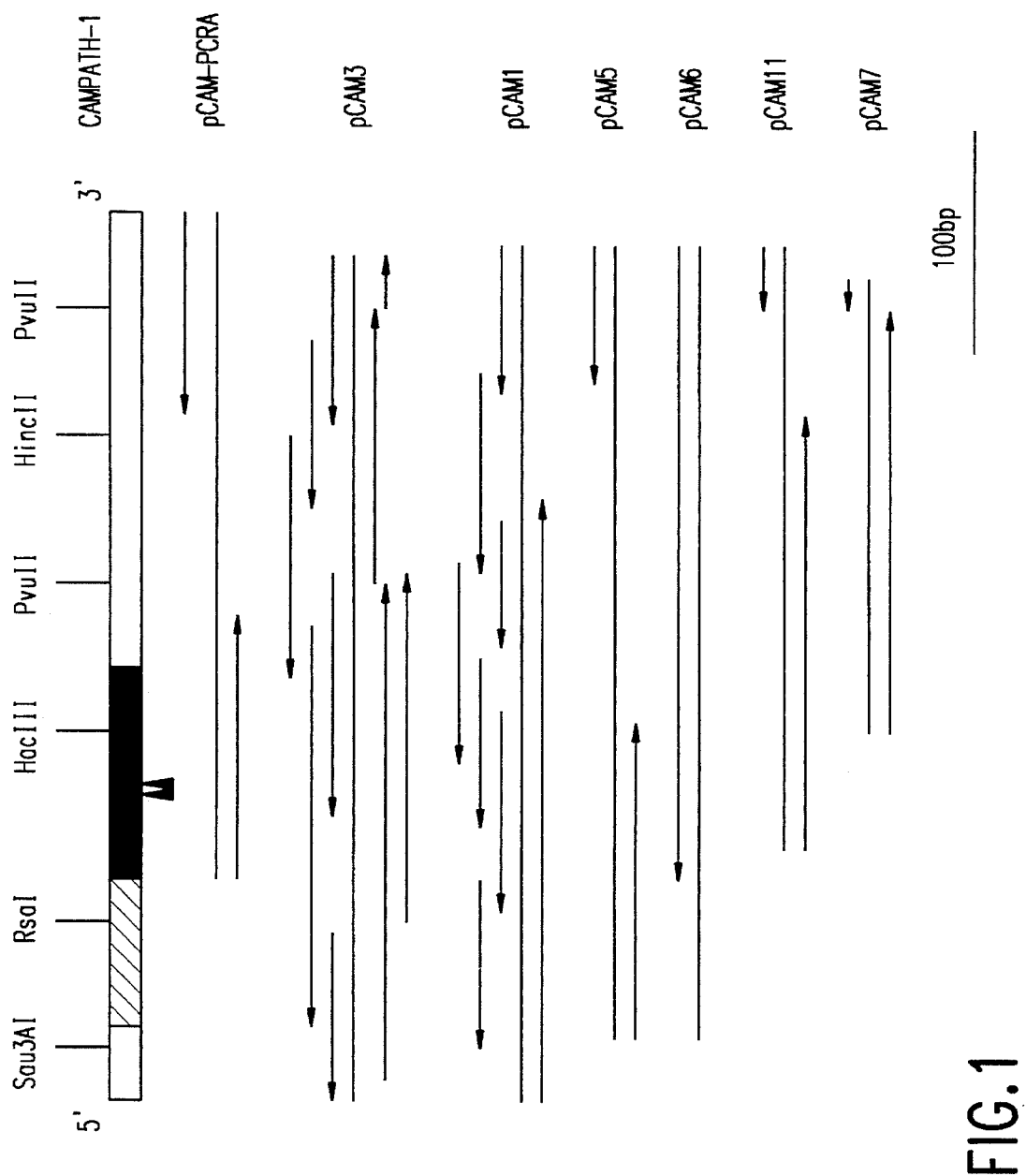

United States Patent [19]

Hale et al.

[11] Patent Number: 5,494,999
[45] Date of Patent: Feb. 27, 1996

[54] SYNTHETIC CDW52(CAMPATH-1) PEPTIDE ANTIGEN

[76] Inventors: Geoffrey Hale; Masahide Tone; Meng-Qi Xia, all of Cambridge University Department of Pathology, Immunology Division, Tennis Court Road, Cambridge, United Kingdom, CB2 1QP

[21] Appl. No.: 137,016

[22] PCT Filed: Apr. 16, 1992

[86] PCT No.: PCT/GB92/00705

§ 371 Date: Oct. 15, 1993

§ 102(e) Date: Oct. 15, 1993

[87] PCT Pub. No.: WO92/18530

PCT Pub. Date: Oct. 29, 1992

[30] Foreign Application Priority Data

Apr. 16, 1991 [GB] United Kingdom ............... 9108056

[51] Int. Cl.$^6$ ........................................................ C07K 7/08
[52] U.S. Cl. ........................................... 530/326; 530/327
[58] Field of Search ..................................... 570/326, 327

*Primary Examiner*—Charles L. Patterson, Jr.
*Attorney, Agent, or Firm*—Rothwell, Figg, Ernst & Kurz

[57] ABSTRACT

A synthetic antigen having the amino acid sequence Gly-Gln-Asn-Asp-Thr-Ser-Gln-Thr-Ser-Ser-Pro-X wherein X is Ser, Ser-Ala, Ser-Ala-Ser, Ser-Ala-Ser-Ser, Ser-Ala-Ser-Ser-Asn, Ser-Ala-Ser-Ser-Asn-Ile, Ser-Ala-Ser-Ser-Asn-Ile-Ser, or an antigenic fragment thereof, a process of the production of the antigen and the use of the antigen in assaying for purifying or inducing CDw52 antibody.

2 Claims, 1 Drawing Sheet

SYNTHETIC CDW52(CAMPATH-1) PEPTIDE ANTIGEN

This invention relates to a synthetic antigen which may be used in assaying for, purifying or inducing CDw52 antibody.

The CAMPATH-1 family of monoclonal antibodies recognise an antigen expressed on the majority of human lymphocytes and monocytes [1–3, "CAMPATH" is a Registered Trade Mark]. At the fourth leucocyte workshop these antibodies were given the provisional designation CDw52 [4]. The antigen is an unusually good target for complement-mediated attack [1,5]. For this reason the IgM antibody, CAMPATH-1M, has been widely used for removal of T lymphocytes from donor bone marrow to prevent graft-versus-host disease [6,7].

The CDw52 antigen is expressed in most cases of lymphoid malignancy [8,9]. Serotherapy of lymphoma and leukaemia with CAMPATH-1 antibodies has therefore been attempted. The rat IgG2b, CAMPATH-1G, which activates both complement and cell-mediated killing, was found to be rather effective in this setting [9,10]. Recently, a human IgG1 antibody (CAMPATH-1H) with the same specificity has been constructed by genetic engineering [11] and this could be administered for a longer period and produced even better clinical results [12].

It is apparent that not all differentiation or tumour associated antigens are equally good targets for serotherapy and the reasons why the CAMPATH-1 antigen is so good are not yet clear. Its abundant expression [5] and lack of modulation [2] are probably relevant factors but knowledge of its structure would give use helpful clues.

About 50% of the CAMPATH-1 antigen could be removed from peripheral blood lymphocytes by treatment with glycosylphosphatidylinositol (GPI)-specific phospholipase C (from *B. thuringiensis*) [3]. This shows that at least some of the antigen is anchored by GPI and possibly all of it since a similar partial resistance has been observed with other GPI-linked antigens [13,14].

The CAMPATH-1 antigen can be extracted from cell homogenates into the aqueous phase of a chloroform:methanol:water system [3] and it can be detected by Western blotting as a broad band of apparent molecular weight 21–28 kD. Treatment with N-glycanase reduces the apparent molecular weight to about 6 kD but the antigenicity is not diminished. The molecule is resistant to treatment with narrow specificity proteases but treatment with broad specificity proteases reduces its apparent molecular weight substantially without affecting antigenicity. However, the antigen is very sensitive to treatment with mild alkali [3].

Antigen extracted from human spleens with chloroform/methanol could be further purified by affinity chromatography using the CAMPATH-1 antibodies. We have now used this purified antigen as the starting point for studies leading to the characterisation of the primary structure of the peptide backbone of CDw52 antigen. A synthetic peptide having the amino acid sequence of the peptide backbone of CDw52 antigen, or an antigenic fragment thereof, may be used to assay for, purify or induce CDw52 antibody.

Accordingly, the present invention provides a peptide having the amino acid sequence as set forth in SEQ ID NO: 1 to 7 or an antigenic fragment of the said peptide. The antigenic fragment may be from 2 to 6 amino acid residues long, for example, 2,3,4,5 or 6 amino acid residues long.

The peptide or antigenic fragment constitute a synthetic antigen. The peptide or fragment thereof may be chemically synthesised from single amino acids and/or preformed peptides of two or more amino acid residues. Solid phase or solution methods may be employed.

The synthetic antigen may be used in a simple and reliable assay for concentration. Many types of assay may be used, for example the antigen may be coupled to plastic microtitre plates and the binding of antibody may be determined using an enzyme-labelled antiglobulin. An assay based on synthetic antigen may be useful for quality control tests during the production of antibody and also for measuring the levels of CAMPATH-1 antibodies in patients serum.

The invention therefore further provides a method of assaying CDw52 antibody in a sample, which method comprises contacting the sample with a peptide or fragment thereof according to the invention and determining whether antibody has bound to the sad peptide or fragment thereof. The method may be used to detect CDw52 antibody or to provide a semi-quantitative or quantitative determination of the amount of such antibody in a sample.

The sample may be a serum sample. The peptide or fragment thereof may be immobilised on a solid support. Binding of CDw52 antibody to the peptide or peptide fragment may be determined using a labelled antiglobulin such as an enzyme-labelled antiglobulin. A substrate for the enzyme would need to be added in that event. The assay may be a simultaneous or sequential assay.

The invention further provides a test kit suitable for use in such an assay, which kit comprises:

(a) a peptide or fragment thereof according to the invention; and (b) means for determining whether, in use, CDw52 antibody in a sample has bound to the peptide or fragment thereof.

In another aspect, the invention provides a process for the purification of CDw52 antibody from a crude preparation thereof, which process comprises passing the crude preparation over a solid support carrying a peptide or fragment thereof according to the invention and eluting the CDw52 antibody which has bound to the said support.

The synthetic antigen may therefore be used for the affinity purification of CDw52 (CAMPATH-1) antibody. For example, it may be coupled to a solid support and crude antibody preparations may be passed over it. Only antibody should bind and it could be eluted by a change in conditions, eg a shift of pH.

The synthetic antigen consequently may be used for selection of variants of CDw52 (CAMPATH-1) antibodies with higher affinity. Two complementary types of approach may be envisaged. Either may be realised using any of a number of different systems for creating large numbers of genetic variants and expressing them. First the new assay method may be used with fragments of low affinity under conditions where the parental antibody gives marginal binding to identify mutants with superior binding ability. Second the affinity columns could be used to directly select cells or microorganisms expressing antibody mutants of higher affinity.

According to the present invention, there is provided a process for the preparation of a CDw52 antibody, which process comprises immunising a mammal with a peptide or fragment thereof according to the invention.

Further, an immortalized cell line which produces a monoclonal CDw52 antibody may be prepared according to the invention by a process which comprises immunising a mammal with a peptide or fragment thereof according to the invention; fusing cells of lymphoid origin from the immunised mammal with cells of an immortalising cell line; and selecting thus-immortalised cells which produce CDw52 antibody. The selected immortalised cell line which produces CDw52 antibody is grown to obtain monoclonal CDw52 antibody.

The peptide or fragment thereof may be administered as a conjugate in which the peptide or peptide fragment is coupled, for example via a side chain of one of the amino acid residues, to a suitable carrier. The carrier molecule is typically a physiologically acceptable carrier. Such conjugates also form part of the invention.

Conventional ways may be used to produce antisera or monoclonal antibody (Kohler and Milstein, Nature, 256, 495–497, 1975). Hydridoma cells producing monoclonal antibody may be prepared by fusing spleen cells from an immunised animal with a tumour cell. The mammal which is immunised may be a rat or mouse. The hydridomas may be grown in culture or injected intraperitoneally for formation of ascites fluid or into the blood stream of an allogenic host or immunocompromised host. Human antibody may be prepared by in vitro immunisation of human lymphocytes with respect to the peptide or a fragment thereof, followed by transformation of the lymphocytes with Epstein-Barr virus.

Antibody may then be isolated. A pharmaceutical composition may be formulated which comprises a pharmaceutically acceptable carrier or diluent and, as active ingredient, CDw52 antibody prepared according to the invention.

Antibody variants, for example having a higher affinity, may be prepared using techniques described in Proc. Natl. Acad. Sci. USA, 86, 5728–5732, 1989 and Science, 246, 1275–1281, 1989. mRNA is isolated from a B cell population, for example spleen or lymph node, from a mammal which produces CDw52 antibody. The mammal may be a rat, mouse or human. Heavy and light chain immunoglobulin cDNA expression libraries are created in bacteriophage lambda vectors. The libraries are screened separately or cross-screened for dual expression of heavy and light chains. After infection of a host such as E. coli, lambda or excised plasmid libraries are screened for antibody molecules specific for CDw52.

In the sequence listing, there are listed SEQ ID NO: 1 to 13 to which reference is made in the description and claims.

The following Example illustrates the invention. In the accompanying Figures:

FIG. 1 shows the restriction map and sequencing strategy of CAMPATH-1 cDNA. The dotted and dark portions on the restriction map indicate the signal peptide sequence and the protein coding region of the CAMPATH-1 antigen respectively. The location and relative length of the individual cDNA inserts are shown by solid lines. Arrows show the direction and relative length of sequence determined. The closed triangles indicate the positions of nucleotide substitutions in the cDNA insert of pCAM1.

EXAMPLE

1. Materials and Methods Antibodies and cells

The CDw52 rat monoclonal antibodies CAMPATH-1M and CAMPATH-1G were variants derived from the hybridoma clones YTH66.9 (IgM) and YTH34.5 (IgG2a), originally made by fusing the myeloma line Y3/Ag1.2.3 with spleen cells from a rat immunised with human T lymphocytes [1]. CAMPATH-1M is a variant of YTH66.9 which has lost the Y3 light chain and CAMPATH-1G is an IgG2b switch variant of YTH34.5 which also lacks the Y3 light chain [16]. Antibodies were purified from ascitic fluid or culture supernatant by precipitation with ammonium sulphate. The K422 cell line [15] was kindly given by Dr M. J. S. Dyer. It was cultured in Iscove's modified Dulbecco's medium supplemented with 5% foetal calf serum. Human splenic tissue was supplied by Mr P Friend (Department of Surgery, University of Cambridge).

Extraction and purification of the CAMPATH-1 antigen

The method originally devised for extraction of gangliosides [17] proved to be very effective for the initial purification of the antigen. The procedure was carried out at room temperature. Fresh or frozen human spleens were homogenised with three vols of water (the weight of tissue in g was taken as one vol in ml). The homogenate was added, with stirring, to 11 vols of methanol and then 5.4 vols of chloroform was added. After stirring for 30 min, the mixture was filtered through Whatman 113V paper, and the residue discarded. Then 3.5 vols of water was added, the mixture was stirred for 10 min and then allowed to stand for at least 1h until the two phases had separated. The upper (aqueous) phase was collected and evaporated to dryness using a rotary evaporator at 40° C. (Alternatively, we found it equally satisfactory to allow the solvent to evaporate from a beaker at room temperature in a fume cupboard over several days.) The residues was resuspended in water and dialysed against water to remove low molecular weight contaminants. This concentrated crude spleen extract was used for affinity purification or other analyses.

CAMPATH-1G (rat IgG2b) was coupled to 3 g or CNBr-activated Sepharose 4 B (Pharmacia) at the ration 5–8 mg protein per ml swollen gel, according to the manufacturer's instructions. Spleen extract was solubilised with 2% sodium deoxycholate in phosphate buffered saline (PBS), precleared with an irrelevant antibody-coupled Sepharose and then mixed with 10 ml of CAMPATH-1G-coupled Sepharose by gentle rotation for 2 h at room temperature (or 16 h at 4° C.). The Sepharose was then packed into a column and washed thoroughly with PBS containing 0.5% sodium deoxycholate and eluted with 50 mM diethylamine pH 11.5 containing 0.5% sodium deoxycholate. The eluate was collected, neutralised with HCl and dialysed against PBS and water.

Enzyme-linked assay for CAMPATH-1 antigen

Doubling dilutions of antigen samples were made in methanol in flat bottomed microtitre plates (Falcon) and the solvent was allowed to evaporate at 37° C. The plates were blocked overnight at 4° C. with 0.1 ml of PBS containing 2% bovine serum albumin (BSA), 20% heat-inactivated normal rabbit serum and 0.02% sodium azide (blocking buffer). Biotinylated CAMPATH-1M (50 μm at 200 μg/ml) was added and incubated at room temperature for 30 min. The plates were washed with PBS containing 0.05% Tween-20 and then incubated for 30 min with 50 μl of a complex of streptavidin and biotinylated horseradish peroxidase (Amersham) diluted 1 in 500 in PBS containing 0.1% BSA. The plates were again washed and the colour was developed with o-phenylenediamine and measured at 495 nm.

Treatment of cells with PI-PLC

About $4 \times 10^6$ K422 cells were incubated for 90 min at 37° C. in a final volume of 150 μl PBS containing 0.1 U/ml B. thuringiensis phosphatidylinositol-specific phospholipase C (PI-PLC) (ICN) together with a cocktail of protease inhibitors: 0.5 mM EDTA, 50 μg/ml PMSF 5 μg/ml pepstatin, 5 μg/ml leupeptin and 5 μg/ml antipain. Control cells were incubated under identical conditions but without the PI-PLC. After treatment, the cells were washed with PBS containing 0.1% BSA and 0.02% sodium azide before immunofluorescence analysis using a variety of monoclonal antibodies followed by FITC-labelled anti-(rat Ig) [1]. The cells were fixed with formaldehyde and analysed with a cytofluorograph (Ortho Model 50H).

Digestion of purified antigen with N-glycanase

Peptide: N-glycosidase F ("N-glycanase" from Genzyme) was used essentially according to the manufacturer's instructions but a cocktail of protease inhibitors was also included. Samples of the purified CAMPATH-1 antigen were first boiled for 3 min in 0.5% SDS containing 0.1M 2-mercaptoethanol. Digestion with N-glycanase was carried out at 37° C. in 275 μl of 0.2M sodium phosphate buffer pH 8.3, containing 0.17% SDS, 1.25% NP40, 10 mM 1,10 phenanthroline hydrate, inhibitor cocktail as above, and 5 units/ml N-glycanase. Samples were taken at various times, and then kept frozen until analysis by SDS gel electrophoresis and Western blotting or ELISA.

Treatment of antigen with alkali

Spleen extract was incubated in 0.05M NaOH at 37° C. Samples were taken at various times and neutralised by addition of 4M acetic acid, then analysed by SDS gel electrophoresis and Western blotting or ELISA.

SDS polyacrylamide gel electrophoresis and Western blotting

Antigen samples were electrophoresed on SDS polyacrylamide gels according to the method of Laemmli [18]. A reducing agent (2-mercaptoethanol) was always included in the sample buffer although omitting it made no difference. The gel not stained but immediately used for Western blotting using polyvinylidene difluoride (PVDF) or nylon transfer membrane. Electrophoretic transfer was carried out using a semi-dry blot apparatus in a buffer containing 39 mM glycine, 48 mM Tris, and 4% methanol at a current density of 0.8 mA/cm$^2$ for at least 1 h. Immunostaining was carried out as follows. The membrane was first blocked with blocking buffer for 2 h. It was then immersed in CAMPATH-1G (100 μg/ml in blocking buffer) for 30 min. washed with PBS containing 0.1% BSA and incubated with peroxidase-coupled anti-(rat Ig) for 30 min. It was washed again and enzyme substrate was added (100 ml of PBS containing 50 mg diaminobenzidine, 30 mg ammonium nickel sulphate, 30 mg cobaltous chloride, and 30 μl of 30% hydrogen peroxide). As soon as the colour developed the membrane was rinsed and dried.

To isolate deglycosylated antigen for protein sequencing, the N-glycanase treated antigen was electrophoresed on a 15% gel and transferred as described above, except that three layers of membrane were used. The third membrane (most distant from the gel) was nylon. This allowed detection of material which had passed through two PVDF membranes. This membrane was immunostained to show the position of the antigen on the first two layers, from which the appropriated regions were excised and used for sequence analysis.

Protein microsequencing

Protein sequence analysis of antigen electroblotted to PVDF membrane and affinity purified material was carried out using an Applied Systems Model 477A pulsed-liquid protein sequencer.

Affinity purified antigen (about 80 pmol, freeze dried) was redissolved in 15 μl of trifluoroacetic acid and applied to a glass fibre filter coated with Biobrene, which had been precycled according to the manufacturer's instructions. Strips of unstained PVDF membrane bearing bound antigen were 'feathered' with a scalpel blade and placed as a single layer into the reaction cartridge of the sequencer, on top of a precycled Biobrene glass-fibre disc. Sequence analysis was performed using modified NORMAL-1 cycles with the cleavage time increased to a standard value of 500 s. Identification of the phenylthiohydontoin (PTH)-amino acids was via an on-line model 120A PTH-amino acid analyser.

Polymerase chain reaction (PCR)

The polymerase chain reaction was carried out according to the MOPAC (mixed oligonucleotides primed amplification of DNA) method [19].

Mixed oligonucleotide primers to amplify the cDNA were synthesised by an automated DNA synthesiser (Applied Biosystems model 381A) according to the determined amino acid sequence. Primer A, (SEQ ID NO: 8) GG(GATC)CA(AG)AA(TC)GA(TC)AC was based on the N-terminal amino acid sequence GQNDT. Primer B1, (SEQ ID NO: 9) GA(TC)AC(GATC)TC(GATC)CA(AG)AC, and primer B2, (SEQ ID NO: 10) GA(TC)AC(GATC)AG(TC)CA(AG)AC, were based on residues 4 to 8 (DTSQT). Four Ser codons (TCG, TCA, TCT, TCC) and two Ser codons (AGT, AGC) were used to design primers B1 and B2 respectively. Each of these primers was used in turn together with an oligo(dT) primer, (Seq ID NO. 11) GACTCGAGTCGACAGCTGCAG(T)$_{17}$, which contained XhoI, SalI PvuII and PstI restriction enzyme sites.

Total RNA from the human B cell line K422 was heated at 65° C. for 3 min and the first strand cDNA was synthesised using an oligo(dT) primer. The reaction contained, in a total volume of 50 μl, 50 mM Tris-HCl ph 8.3, 75 mM KCl, 1 mM DDT, 15 mM MgCl$_3$, 1 mM of each dNTP, 400 ng oligo(dT), 20 μg total RNA from K422 cells, 5 units of ribonuclease inhibitor RNasin and 40 units of reverse transcriptase. This mixture was incubated at 42° C. for 2 hours and then the mRNA:cDNA duplex was recovered by ethanol precipitation.

The first strand cDNA was amplified by PCR using primer A and the oligo(dT) primer in a reaction volume of 100 μl containing 10 mM Tris-HCl pH 8.3, 50 mM KCl, 1.5 mM MgCl$_3$, 0.01% gelatine, 0.2 mM of each dNTP, 100 pmol primer A, 120 pmol oligo(dT) primer and all of the first strand cDNA. After heating at 95° C. for 2 min, 8 units of Taq polymerase (Koch Light) was added and the mixture was subjected to 30 rounds of temperature cycles. Each cycle was 30 s at 95° C., 30 s at 37° C. and 1 min at 72° C. Finally the mixture was incubated at 50° C. for 10 min. The amplified PCR product was separated from the primers by QIAGEN tip and re-amplified using the oligo(dT) primer with either primer B1 or B2. Half of the PCR product was added to each reaction mixture in a final volume of 100 μl under similar conditions to the above, but only 50 μl of each reaction mixture was subjected to temperature cycling and the rest was used as a control. The amplified PCR products were analysed by 2% agarose gel electrophoresis.

cDNA cloning and nucleotide sequencing

The 350 bp DNA fragment amplified by PCR using primer A and oligo(dT) primer was isolated from a 2% agarose gel and repaired with Klenow fragment. After purification, the DNA fragment was digested with XhoI (the oligo(dT) primer had an XhoI site) and introduced into the HincII-XhoI site of PHSG397 [20]. One positive clone was obtained and named pCAM-PCRA.

A cDNA library was constructed using the lambda-gt10 cloning vector and poly(A)–RNA from K422 cells. About 8×10$^4$ independent plaques were screened using $^{32}$p-labelled 350 bp HindIII-XhoI fragment from PCAM-PCRA. Hybridization was carried out at 42° C. for 40 hours in a solution containing 50% formamide, 0.9M NaCl, 50 mM sodium phosphate pH 7.4, 5 mM EDTA, 10× Denhardt's solution, 0.1% SDS and 100 μg/ml denatured salmon sperm DNA. The filters were washed with 1×SSC at 65° C. Positive plaques were purified under similar conditions.

Phage DNAs from positive clones were digested with EcoRI and the cDNA inserts were subcloned into the EcoRI sites of the plasmid vector PUC18. Nucleotide sequences were determined by the dideoxy chain-termination method using PUC18, PHSG396 [20] and/or M13mp18. Deletion mutants of pCAM1 and pCAM2 were constructed by the exonuclease III method [21] and EcoRI-RsaI, RsaI-PvuII, PvuII-EcoRI and PvuII fragments were subcloned into the plasmid vector PHSG396 for nucleotide sequencing.

RNA purification and Northern blot analysis

Total RNA was isolated from K422 cells by the quanidinium chloride method [22]. Poly(A)– RNA was purified by affinity chromatography on poly(U) Sepharose. For Northern blotting, 10 μg of total RNA and 0.5 μg of poly(A)– were electrophoresed through a 1.5% agarose/formamide gel and transferred to a nylon membrane. The RNA filter was hybridized with $^{32}$p-labelled CAMPATH-1 antigen cDNA (pCAM2) and washed with 0.5×SSC/0.1% SDS at 65° C.

2. Results

Purification of CAMPATH-1 antigen and studies on the nature of its antigenic epitope.

In a typical experiment, CAMPATH-1 antigen was extracted from a single human spleen (mass about 210 g) and purified in three passes over an affinity column consisting of 10 ml of CAMPATH-1G-coupled Sepharose. The total yield of antigen, estimated by inhibition of an ELISA assay [23] was approx. 40 nmol, which compares with the expected yield of about 100 nmol assuming that there are about 5×10$^5$ antigen molecules per cell [5] and about 5×10$^8$ lymphocytes per g.

The heat stability of purified antigen was tested by heating samples, dissolved in water to 100° C. for 20 min or autoclaving at 121° C. for 15 min, followed by rapid cooling on ice. Neither treatment affected the antigenicity detected by ELISA assay; if anything the titre of the heat-treated antigen was increased compared with an untreated control.

Samples of affinity-purified CAMPATH-1 antigen from spleen were digested for up to 20 h with N-glycanase and analysed by SDS gel electrophoresis and immunoblotting. A broad band at about 21–28 kD in the untreated sample was soon converted into a much smaller, but still apparently heterogenous band of approx 6 kD without the appearance of substantial amounts of intermediate species. This result suggests that only one glycosylation site sensitive to N-glycanase is present, though it is possible that there are two or more sites which exhibit substantial cooperativity in the rate of enzymic cleavage.

In a parallel experiment, samples of CAMPATH-1 antigen were treated with 50 mM NaOH for up to 26 h and analysed in the same way. This time the antigenic activity was lost with time and no smaller fragments could be detected by immunoblotting. The same result was obtained when 2M sodium borohydride was included in the incubation during the incubation. These results could be explained if the antigenic epitope is part of an O-linked oligosaccharide which is not detected by these assays even if it is protected from the alkaline peeling reaction by the presence of borohydride. However, we cannot exclude other alkali-labile structures.

CAMPATH-1 antigen from K422 cells: comparison with antigen from spleen cells and sensitivity to PI-PLC The cell line K422, established from a patient with non-Hodgkin's lymphoma was found to express substantial amounts of CAMPATH-1 antigen [15]. This made it potentially useful for many experiments including the construction of a cDNA library. The following experiments were carried out to check whether the antigen was similar to that expressed by normal lymphocytes.

CAMPATH-1 antigen was extracted from approximately 2×10$^8$ K422 cells with chloroform/methanol. The yield was comparable with that from normal lymphocytes. Samples of the extracts were found to be similar when analysed by SDS gel electrophoresis and immunoblotting.

It was previously shown that the CAMPATH-1 antigen on peripheral blood lymphocytes can be partially cleaved by PI-PLC [3]. A similar experiment was now carried out using K422 cells and extra precautions were taken to avoid possible artefacts due to protease contamination of the PIPLC. K422 cells were treated with the enzyme, or with buffer alone, in the presence of a cocktail of protease inhibitors and then analysed by indirect immunofluorescence using CAMPATH-1, CD45 or CD59 antibodies. The CD45 antigen was chosen as a negative control because it is known to have a conventional protein anchor and the CD45R epitope is particularly sensitive to proteolytic cleavage [24]. The CD59 antigen was chosen as a positive control because it is a known GPI anchored protein [25] and is expressed on K422 cells.

It was found that the binding of CAMPATH-1 and CD59 antibodies were both reduced significantly, though not completely, while the binding of the CD45 and CD45R antibodies was unaffected or even slightly increased. This result implies that at least a proportion of the CAMPATH-1 antigen (and possibly all) is GPI anchored in K422 cells.

Protein sequence of the CAMPATH-1 glycoprotein

From the affinity purified CAMPATH-1 antigen, the following N-terminal sequence was obtained:

Gly-Gln-?-Asp-Thr-Ser-Gln-Thr-Ser-Ser-Pro (SEQ ID NO: 12) Consistent results were obtained from several sequencer runs, but on no occasion were any other amino acids detected after Pro-11 although up to 20 degradation cycles were carried out. The amount of N-terminal glycine (55 pmol) was consistent with the amount of antigen used for sequencing (80 pmol), estimated by inhibition of an ELISA assay. Alkylation of reduced CAMPATH-1 antigen with iodoacetic acid failed to generate a PTH-CmCys signal on cycle 3 so it was unlikely that residue 3 was a cysteine.

To determine whether the third residue might be an N-linked glycosylation site, a sample of affinity purified CAMPATH-1 antigen was treated with N-glycanase for 22 h, separated by SDS gel electrophoresis, transferred to a PVDF membrane and localised by immunostaining of a duplicate membrane. The apparent molecular weight was substantially reduced from 21–28 kD to about 6 kD. Five cycles of Edman degradation were carried out on the membrane containing the deglycosylated antigen and the same sequence was found except that the third residue was Asp. N-glycanase treatment would hydrolyse the N-glycosidic bond between Asn and N-acetylglucosamine to Asp so we believe that residues 3–5 are Asn-Asp-Thr which form an N-glycosylation site.

At this stage we could not be sure what sequence might be present after Pro-11. Results from the Edman degradation were strongly suggestive that the end of the peptide had been reached since background levels of amino acids remained low and no fresh N-terminus could be obtained by treatment with cyanogen bromide.

Amplification of cDNA using the polymerase chain reaction

Because there are three Ser residues in the 11 amino acid N-terminal sequence and each could correspond to any of six DNA codons, oligonucleotides made according to this information will be very degenerate and poor probes for cDNA screening. The best region of the sequence was from residues 1 to 5 (GQNDT) according to which a 32-fold degenerate 14-mer (primer A) was made. One attempt to isolate cDNA clones using this as a hybridisation probe was unsuccessful so we adopted a different approach using the polymerase chain reaction to amplify the desired cDNA. Since a specific primer was only available for one end of the sequence, we had to use an oligo(dT) primer at the 3' end. To minimise the chances of amplifying irrelevant sequences we introduced a second round of amplification using different 5' primers based on residues 4–8 (DTSQT). Four Ser codons were used in primer B1 and two in primer B2 so they consisted of 64 and 32 different 14-mers respectively.

Total RNA from K422 cells was used as a template for synthesis of the first strand cDNA used in the subsequent polymerase chain reaction. Four major bands (510 bp, 470 bp, 440 bp, 350 bp) were observed by 2% agarose gel electrophoresis after the first PCR amplification (primers A and oligo(dT)). The primers were removed and the PCR product was amplified again using oligo(dT) with either primer B1 or primer B2. The resulting products differed from the products of the first reaction in only the smallest (350 bp) band which was present in the amplified product of primer B2 but not in that of B1. We concluded that the other three bands might be artefacts caused by non-specific priming but that the 350 bp PCR product might be the authentic cDNA since unique sequence primers for the CAMPATH-1 antigen were included in primer A and either primer B1 or B2 (but not both).

The 350 bp fragment amplified with primers A and oligo(dT) was isolated from the agarose gel and cloned into the pHSG397 cloning vector. The nucleotide sequence of the inserted fragment of the positive clone pCAM-PCRA was partially determined from both ends. The deduced six amino acid residues downstream of the primer A binding site agreed exactly with the protein sequence data. This fragment was then used as a hybridisation probe to isolate clones from a K422 cDNA library.

Isolation of cDNA clones and sequence analysis

A cDNA library constructed from the K422 cell line was screened with $^{32}$P-labelled 350 bp fragment from PCAM-PCRA. Six positive clones were isolated and these inserts were subcloned into EcoRI sites of pUC18 and M13mp18. Nucleotide sequences of these clones were partially determined from both ends. Their lengths and the overall sequencing strategy are shown in FIG. 1.

The entire nucleotide sequences of the cDNA inserts of pCAM1 and pCAM2 were determined and their lengths were found to be 443 bp and 433 bp respectively. The cDNA hybridised to an RNA molecule of approx 580 bp by Northern blot analysis. Thus the total cDNA sequence accounts for about 76% of the full-length RNA.

The nucleotide sequence of the cDNA insert of pCAM2 is shown in SEQ ID NO: 13. A polyadenylation signal AATAAA is located at nucleotide position 417 to 422. Two long open reading frames can be observed at nucleotide positions 1 to 221 and 1 to 216. The N-terminal Gly is found in the second of these reading frames with Met residues positioned 24 and 9 residues before it. The first Met is a plausible initiation site and so the CAMPATH-1 antigen encoded by our cDNA clones consists of 37 amino acid residues with a probable leader sequence of 24 amino acids residues. This leader sequence consists of typical hydrophobic amino acids and ends at a plausible scission point.

The 37 residue peptide which begins at the N-terminal Gly consists of a 20 residue hydrophilic section followed by a 17 residue hydrophobic section. Two potential N-linked glycosylation sites (NDT and NIS) are found in the hydrophilic section as well as 9 Ser or Thr residues which could be O-linked glycosylation sites. The C-terminal section comprises hydrophobic residues with a strong propensity to form an alpha helix and is similar to the membrane spanning domains which are cleaved from the C-terminus of GPI-anchored proteins.

Two nucleotide substitutions were found between pCAM1 and pCAM2, between positions 151–156 where pCAM1 has the sequence AGCATG coding for Ser-Met, whereas pCAM2 has AACATA coding for Asn-Ile. One of the cDNA clones (pCAM7) was truncated at the 5' end so it lacked that part of the sequence but the three other clones (pCAM5, pCAM6 and pCAM11) and the clone obtained from the PCR product (pCAM-PCRA) all aligned with pCAM2. These substitutions might be a cloning artefact, but if not, the protein variant coded by pCAM1 could have some significance since the region affected is a potential N-linked glycosylation site as well as lying very close to the likely site of attachment of the GPI anchor.

No other DNA or protein sequences have been found with significant homology to pCAM2 or the amino acid sequence of the CAMPATH-1 antigen deduced from it. Current versions of EMBL, GENBANK, and NBRL DNA databases and the Doolittle, PIR, PseqIP and Swiss-Prot protein databases were searched during January 1991 using the FASTA analysis programme [26].

References

1. Hale, G., Bright, S., Chumbley, G., Hoang, T., Metcalf, D., Munro, A. J., Waldmann, H., *Blood* 1983. 62, 873.
2. Hale, G., Hoang, T., Prospero, T., Watt, S. M., & Waldmann, H., *Mol. Biol. Med.* 1983. 1, 305.
3. Hale, G., Xia, M-Q., Tighe, H. P., Dyer, M. J. S., & Waldmann, H., *Tissue Antigens* 1990. 35, 118.
4. Schmidt, R. E., *Leucocyte Typing IV* (ed Knapp, W., Dorken, B., Gilks, W. R., et al), pub OUP 1989. p 517.
5. Bindon, C. I., Hale, G., & Waldmann, H., *Eur. J. Immunol.* 1988. 18, 1507.
6. Waldmann, H., Or, R., Hale, G., Weiss, L., Cividalli, G., Samuel, S., Manor, D., Brautbar, C., Polliack, A., Rachmilewitz, E. A., & Slavin, S., *Lancet* 1984. 2, 483.
7. Hale, G., Cobbold, S., Waldmann, H., *Transplantation*, 1988. 45, 753.
8. Hale, G, Swirsky, D., Waldmann, H., & Chan, L. C., *Brit. J. Haematol.* 1985. 60, 41.
9. Dyer, M. J. S., Hale, G., Marcus, R., & Waldmann, H. *Leukaemia and Lymphoma* 1990. 2, 179.
10. Dyer, M. J. S., Hale, G., Hayhoe, F. G. J., & Waldmann, H., *Blood* 1989. 73, 1431.
11. Riechmann, L., Clark, M. R., Waldmann, H., & Winter, G., *Nature* 1988. 332, 323.
12. Hale, G., Dyer, M. J. S., Clark, M. R., Phillips, J. M., Marcus, R., Riechmann, L., Winter, G., & Waldmann, H., *Lancet* 1988. 2, 1394.
13. Low, M. G., & Kincade, P. W. *Nature* 1985. 318, 62.
14. Ferguson, M. A., & Williams, A. F., *Annu. Rev. Biochem.* 1988. 57, 497.
15. Dyer, M. J. S., Fischer, P., Nacheva, E., Labastide, W., & Karpas, A. *Blood* 1990. 75, 709.
16. Hale, G., Cobbold, S. P., Waldmann, H., Easter, G., Matejtschuk, P., & Coombs, R. R. A., *J. Immunol. Meth.* 1987. 103, 59.
17. Svennerholm, L., & Fredman, P., *Biochim. Biophys. Acta* 1980. 617, 97.
18. Laemmli, U. K., *Nature* 1970. 227, 680.
19. Lee, C. C., Wu,X., Gibbs, R. A., Cook, R. G., Muzhy, D. M., & Caskey, C. T., *Science* 1988. 239, 1288.
20. Takeshita, S., Sato, M., Toba, M., Masahashi, W., & Hashimoto-Gotoh, T., *Gene* 1987. 61, 63.

21. Ausubel, F. M., Brent, R., Kingston, R. E., Moore, D. D., Seidman, J. G., Smith, J. A. & Struhl, K. (eds) *Current Protocols in Molecular Biology* pub Wiley 1988.
22. Chirgwin, J. J., Przbyla, A. E., MacDonald, R. J., & Rutter, W. J., *Biochemistry* 1979. 18, 5294.
23. Xia, M-Q., *M.Phil Dissertation*, University of Cambridge, 1989.
24. Hale, G., Buckie, C., Lovat, P., Prospero, T., & Waldmann, H., *Leucocyte Typing III. White cell differentiation antigens* (ed McMichael, A. J.) OUP, Oxford 1987. pp 811.
25. Davies, A., Simmons, D. L., Hale, G., Harrison, R. A., Tighe, H., Lachmann, P. J., & Waldmann, H., *J. Exp. Med.* 1989. 170, 637.
26. Pearson, W. R., & Lipman, D. J. *Proc. Natl. Acad. Sci. USA.* 1988. 85, 2444.

We claim:

1. A peptide having the amino acid sequence as set forth in SEQ ID NO: 1 to 7.

2. A conjugate comprising a peptide as defined in claim 1 coupled to a physiologically acceptable carrier.

\* \* \* \* \*

UNITED STATES PATENT AND TRADEMARK OFFICE
CERTIFICATE OF CORRECTION

PATENT NO. : 5,494,999
DATED : February 27, 1996
INVENTOR(S) : Geoffrey Hale et al.

It is certified that error appears in the above-indentified patent and that said Letters Patent is hereby corrected as shown below:

On the title page, and in column 1, line 2:

The second word in the Title should be replaced with -- CDw52(CAMPATH-1) --; Under the "Foreign Application Priority Data", the U.K. patent number should be -- 9108056.4 --; In the Specification: Col. 4, line 26, "ration" should be -- ratio --; Col. 7, lines 9-10, "quanidinium" should be -- guanidinium --; Col. 9, line 38, "PCAM-" should be -- pCAM- --.

Signed and Sealed this

Thirteenth Day of August, 1996

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 1:

```
Gly Gln Asn Asp Thr Ser Gln Thr Ser Ser Pro Ser
 1               5                   10
```

( 2 ) INFORMATION FOR SEQ ID NO: 2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 2:

```
Gly Gln Asn Asp Thr Ser Gln Thr Ser Ser Pro Ser Ala
 1               5                   10
```

( 2 ) INFORMATION FOR SEQ ID NO: 3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 3:

```
Gly Gln Asn Asp Thr Ser Gln Thr Ser Ser Pro Ser Ala Ser
 1               5                   10
```

( 2 ) INFORMATION FOR SEQ ID NO: 4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 4:

```
Gly Gln Asn Asp Thr Ser Gln Thr Ser Ser Pro Ser Ala Ser Ser
 1               5                   10                  15
```

( 2 ) INFORMATION FOR SEQ ID NO: 5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 5:

```
Gly Gln Asn Asp Thr Ser Gln Thr Ser Ser Pro Ser Ala Ser Ser Asn
 1               5                   10                  15
```

( 2 ) INFORMATION FOR SEQ ID NO: 6:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 6:

```
Gly Gln Asn Asp Thr Ser Gln Thr Ser Ser Pro Ser Ala Ser Ser Asn
 1               5                   10                  15
Ile
```

( 2 ) INFORMATION FOR SEQ ID NO: 7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( x i ) SEQUENCE DESCRIPTION: SEQ ID NO: 7:

```
Gly  Gln  Asn  Asp  Thr  Ser  Gln  Thr  Ser  Ser  Pro  Ser  Ala  Ser  Ser  Asn
 1                   5                        10                       15

Ile  Ser
```

( 2 ) INFORMATION FOR SEQ ID NO: 8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 8:

GGNCARAAYG AYAC            14

( 2 ) INFORMATION FOR SEQ ID NO: 9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 9:

GAYACNTCNC ARAC            14

( 2 ) INFORMATION FOR SEQ ID NO: 10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 10:

GAYACNAGYC ARAC            14

( 2 ) INFORMATION FOR SEQ ID NO: 11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( x i ) SEQUENCE DESCRIPTION: SEQ ID NO: 11:

GACTCGAGTC GACAGCTGCA GTTTTTTTTT TTTTTTT        38

( 2 ) INFORMATION FOR SEQ ID NO: 12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v ) FRAGMENT TYPE: N-terminal ( x i ) SEQUENCE DESCRIPTION: SEQ ID NO: 12:

```
Gly  Gln  Xaa  Asp  Thr  Ser  Gln  Thr  Ser  Ser  Pro
 1              5                         10
```

( 2 ) INFORMATION FOR SEQ ID NO: 13:

( i ) SEQUENCE CHARACTERISTICS:
        ( A ) LENGTH: 433 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v ) FRAGMENT TYPE: internal ( i x ) FEATURE:
        ( A ) NAME/KEY: misc_feature
        ( B ) LOCATION: 1..11
        ( D ) OTHER INFORMATION: /note="N-terminal protein sequence
            as determined by Edman degradation."

( i x ) FEATURE:
        ( A ) NAME/KEY: misc_feature
        ( B ) LOCATION: 152..156
        ( D ) OTHER INFORMATION: /note="Position of nucleotide
            substitution in clone pCAM1 (A to G)"

( i x ) FEATURE:
        ( A ) NAME/KEY: polyA_signal
        ( B ) LOCATION: 417..422

( i x ) FEATURE:
        ( A ) NAME/KEY: misc_feature
        ( B ) LOCATION: 3
        ( D ) OTHER INFORMATION: /note="(Asn-3) N-glycosylation
            site"

( i x ) FEATURE:
        ( A ) NAME/KEY: misc_feature
        ( B ) LOCATION: 16
        ( D ) OTHER INFORMATION: /note="(Asn-16) possible
            glycosylation site"

( i x ) FEATURE:
        ( A ) NAME/KEY: misc_feature
        ( B ) LOCATION: one-of(12, 14, 15, 18)
        ( D ) OTHER INFORMATION: /note="(Ser-12, Ser-14, Ser-15 and
            Ser-18) possible glycosylation sites"

( i x ) FEATURE:
        ( A ) NAME/KEY: misc_feature
        ( B ) LOCATION: 12..15
        ( D ) OTHER INFORMATION: /note="(Ser-12 to Ser-15) likely
            site for attachment of a GPI anchor"

( i x ) FEATURE:
    ( A ) NAME/KEY: CDS
    ( B ) LOCATION: 34..216

( x i ) SEQUENCE DESCRIPTION: SEQ ID NO: 13:

```
TGCTACCAAG ACAGCCACGA AGATCCTACC AAA ATG AAG CGC TTC CTC TTC CTC        54
                                    Met Lys Arg Phe Leu Phe Leu
                                     1               5

CTA CTC ACC ATC AGC CTC CTG GTT ATG GTA CAG ATA CAA ACT GGA CTC        102
Leu Leu Thr Ile Ser Leu Leu Val Met Val Gln Ile Gln Thr Gly Leu
            10                  15                  20

TCA GGA CAA AAC GAC ACC AGC CAA ACC AGC AGC CCC TCA GCA TCC AGC        150
Ser Gly Gln Asn Asp Thr Ser Gln Thr Ser Ser Pro Ser Ala Ser Ser
        25                  30                  35

AAC ATA AGC GGA GGC ATT TTC CTT TTC TTC GTG GCC AAT GCC ATA ATC        198
Asn Ile Ser Gly Gly Ile Phe Leu Phe Phe Val Ala Asn Ala Ile Ile
 40                  45                  50                  55

CAC CTC TTC TGC TTC AGT TGAGGTGACA CGTCTCAGCC TTAGCCCTGT               246
His Leu Phe Cys Phe Ser
                 60

GCCCCCTGAA ACAGCTGCCA CCATCACTCG CAAGAGAATC CCCTCCATCT TTGGGAGGGG      306

TTGATGCCAG ACATCACCAG GTTGTAGAAG TTGACAGGCA GTGCCATGGG GGCAACAGCC      366

AAAATAGGGG GGTAATGATG TAGGGGCCAA GCAGTGCCCA GCTGGGGGTC AATAAAGTTA      426

CCCTTGT                                                                433
```

( 2 ) INFORMATION FOR SEQ ID NO: 14:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Met Lys Arg Phe Leu Phe Leu Leu Leu Thr Ile Ser Leu Leu Val Met
 1               5                  10                  15

Val Gln Ile Gln Thr Gly Leu Ser Gly Gln Asn Asp Thr Ser Gln Thr
                20                  25                  30

Ser Ser Pro Ser Ala Ser Ser Asn Ile Ser Gly Gly Ile Phe Leu Phe
            35                  40                  45

Phe Val Ala Asn Ala Ile Ile His Leu Phe Cys Phe Ser
         50                  55                  60
```